United States Patent
Glennon et al.

Patent Number: 5,969,137
Date of Patent: Oct. 19, 1999

[54] BENZYLAMIDINE DERIVATIVES WITH SEROTONIN RECEPTOR BINDING ACTIVITY

[75] Inventors: Richard A. Glennon, Richmond, Va.; Ho Law, Meylan, France

[73] Assignee: Virginia Commonwealth University, Richmond, Va.

[21] Appl. No.: 08/821,297

[22] Filed: Mar. 20, 1997

Related U.S. Application Data

[63] Continuation-in-part of application No. 08/715,792, Sep. 19, 1996.

[51] Int. Cl.$^6$ .................................................. C07D 239/06
[52] U.S. Cl. ............................................ 544/335; 544/242
[58] Field of Search ...................... 544/242, 335

[56] References Cited

FOREIGN PATENT DOCUMENTS

92/14453  9/1992  WIPO .

OTHER PUBLICATIONS

*The Merck Index*, 11th edition, 1989, p. 1591.
Brimblecome et al., *Br. J. Pharmac.*, 1969, vol. 37, pp. 425–435.
Boudier et al., *Life Sciences*, 1975, vol. 17, No. 3, pp. 377–385.
Jen et al., *Journal of Medicinal Chemistry*, 1975, vol. 18, No. 1, pp. 90–99.
Wentland et al., *J. Med. Chem.*, 1987, vol. 30, pp. 1482–1489.
Schoeffter et al., *European Journal of Pharmacology*, 1991, vol. 196, pp. 213–216.
Huang et al, "synthesis of 2–(benzoylmethylene), etc" CA 108:21818, (1988).

*Primary Examiner*—Patricia L. Morris
*Attorney, Agent, or Firm*—Bacon & Thomas

[57] ABSTRACT

This invention relates to compounds having serotonin receptor binding activity, to pharmaceutical compositions containing them and to their medical use, particularly in the treatment of CNS conditions. Described herein are compounds which have the general formula:

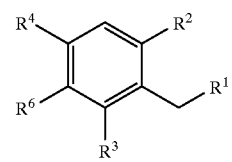

wherein
$R^1$ is selected from a group of Formula i and ii:

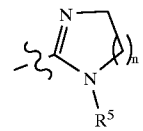

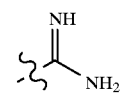

n is 1–3;
$R^2$ is selected from H and $C_{1-6}$alkyl;
$R^3$ is selected from H and $C_{1-6}$alkyl;
$R^4$ is selected from $C_{1-6}$alkyl, halo, phenyl, amino and nitro;
$R^5$ is selected from H, $C_{1-6}$alkyl and arylalkyl;
$R^6$ is selected from H or a alkylene group which is bonded to $R^4$ to form the naphthalene ring skeleton; and salts, hydrates and solvates thereof.

Also described is the use of these compounds as pharmaceuticals to treat indications where stimulation of subtypes of the serotonin receptor is implicated, such as migraine.

8 Claims, No Drawings

BENZYLAMIDINE DERIVATIVES WITH SEROTONIN RECEPTOR BINDING ACTIVITY

This application is a continuation-in-part of U.S. patent application Ser. No. 08/715,792, filed on Sep. 19, 1996.

FIELD OF THE INVENTION

This invention relates compounds having serotonin receptor binding activity, to pharmaceutical compositions containing them and to their medical use, particularly in the treatment of CNS conditions.

BACKGROUND TO THE INVENTION

Through its interaction with receptors borne on neuronal and other cells, 5-hydroxytryptamine (5-HT or serotonin) exerts various physiological effects. Imbalances in this interaction are believed to be responsible for such conditions as anxiety, hallucination, migraine, chemotherapy-induced nausea and for disorders in sexual activity, cardiovascular activity and thermoregulation, among others. From an improved understanding of the 5-HT receptor population, it is apparent that these effects are mediated selectively through individual types and subtypes of the 5-HT receptors. Migraine, for example, has been treated with ergotamine, dihydroergotamine, methylsergide and, most recently, sumatriptan, all of which presumably act at $5\text{-HT}_{1D}$ type receptors. The $5\text{-HT}_{1D}$ receptor is further classified into the subtypes $5\text{-HT}_{1D\alpha}$ and $5\text{-HT}_{1D\beta}$.

Current treatments for migraine, including sumatriptan, continue to have unwanted side effects. These include coronary vasospasm, hypertension and angina. Recent evidence suggests that sumatriptan's contraction of coronary arteries may be mediated by its stimulation of the $5\text{-HT}_{1D\beta}$ subtype of the $5\text{-HT}_{1D}$ receptor (Kaumann, A. J. Circulation, 1994, 90:1141–1153).

Given the physiological and clinical significance of the $5\text{-HT}_{1D}$ receptor, and the potential side effect liability of stimulation of its $5\text{-HT}_{1D\beta}$ subtype, it would be desirable to provide compounds that bind with high affinity to the $5\text{-HT}_{1D\alpha}$ subtype of the $5\text{-HT}_{1D}$ receptor. Such compounds would be medically useful for example to treat indications such as migraine and others for which administration of a $5\text{-HT}_{1D\alpha}$ ligand is indicated. Also they could be used diagnostically, for example to identify these receptors and to screen drug candidates.

SUMMARY OF THE INVENTION

According to one aspect of the invention, there are provided compounds of Formula I and salts, solvates or hydrates thereof:

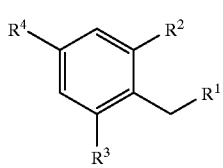

I wherein $R^1$ is selected from a group of Formula i and ii:

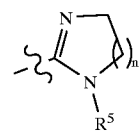

i

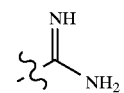

ii n is 1–3;
$R^2$ is selected from H and $C_{1-6}$alkyl;
$R^3$ is selected from H and $C_{1-6}$alkyl;
$R^4$ is selected from $C_{2-6}$alkyl, halo, phenyl, amino and nitro;
$R^5$ is selected from H, $C_{1-6}$alkyl and arylalkyl; and
salts, hydrates and solvates thereof;
with the provisos that
1) $R^4$ is not amino, nitro, halo or $C_2$alkyl when $R^2$ and $R^3$ are both H and $R^1$ is a group of Formula i with n=1 and $R^5$=H;
2) $R^4$ is not halo or nitro when $R^2$ and $R^3$ are both H and $R^1$ is a group of Formula i with n=2 and $R^5$=H; and
3) $R^4$ is not t-butyl when $R^2$ and $R^3$ are both methyl and $R^1$ is a group of Formula i with n=1 and $R^5$=H.

According to another aspect of the invention, there is provided a pharmaceutical composition comprising a compound of Formula II in an amount effective to stimulate the $5\text{-HT}_{1D\alpha}$ receptor selectively over the $5\text{-HT}_{1D\beta}$ receptor, and a pharmaceutically acceptable carrier:

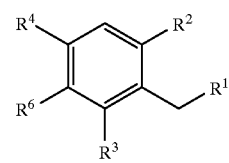

II wherein
$R^1$ is selected from a group of Formula i and ii:

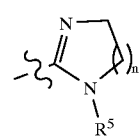

i

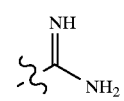

ii n is 1–3;
$R^2$ is selected from H and $C_{1-6}$alkyl;
$R^3$ is selected from H and $C_{1-6}$alkyl;
$R^4$ is selected from $C_{1-6}$alkyl, halo, phenyl, amino and nitro;

$R^5$ is selected from H, $C_{1-6}$alkyl and arylalkyl;

$R^6$ is selected from H or a alkylene group which is bonded to $R^4$ to form the naphthalene ring skeleton; and salts, hydrates and solvates thereof.

In another aspect of the present invention there are provided compositions containing the present compounds either for use as reagents, for example in the identification of 5-$HT_{1D\alpha}$ receptor ligands, or for pharmaceutical use to treat conditions where a 5-$HT_{1D\alpha}$ ligand is indicated. These and other aspects of the present invention are described in greater detail hereinbelow.

DETAILED DESCRIPTION AND PREFERRED EMBODIMENTS

The term "$C_{1-6}$alkyl" as used herein means straight and branched chain alkyl radicals containing from one to six carbon atoms and includes methyl, ethyl, propyl, isopropyl, t-butyl and the like.

The term "$C_{2-6}$alkyl" as used herein means straight and branched chain alkyl radicals containing from two to six carbon atoms and includes ethyl, isopropyl, propyl, t-butyl and the like.

The term "halo" as used herein means halide and includes fluoro, chloro, bromo and iodo.

The term "arylalkyl" as used herein means a five or six membered aromatic or heteroaromatic ring (including phenyl, pyridyl, thiophene and the like) which is attached to a specified node via a $C_{1-3}$alkylene linker.

This invention relates to compounds that bind with at least 10-fold selectivity to the serotonin 5-$HT_{1D\alpha}$ receptor, relative to the serotonin 5-$HT_{1D\beta}$ receptor, as judged by in vitro binding affinities using, for example, the assay exemplified herein. Preferred are those compounds which bind with at least 50-fold selectivity to the serotonin 5-$HT_{1D\alpha}$. Most preferred, are those compounds which bind with at least 100-fold selectivity to the serotonin 5-$HT_{1D\alpha}$ receptor.

In embodiments of the invention, compounds of Formula I and II include those in which $R^1$ is selected from a group of Formula i and ii. In preferred embodiments $R^1$ is a group of Formula i. When $R^1$ is a group of Formula i, compounds of Formula I and II include those in which n is 1, 2 or 3. In preferred embodiments, n is 1 or 2.

In other embodiments of the invention, compounds of Formula I and II include those in which $R^2$ and $R^3$ are selected from H and $C_{1-6}$alkyl. In preferred embodiments, one of $R^2$ and $R^3$ is H and the other is methyl, or $R^2$ and $R^3$ are both methyl.

In other embodiments of the invention, compounds of Formula I and II include those in which $R^4$ is selected from $C_{1-6}$alkyl, halo, phenyl, amino and nitro. In preferred embodiments of the invention, $R^4$ is selected from $C_{1-6}$alkyl and halo. In the most preferred embodiment of the invention $R^4$ is selected from t-butyl and bromo.

In further embodiments of the invention, compounds of Formula I and II include those in which $R^5$ is selected from H, $C_{1-6}$alkyl and arylalkyl. In particular embodiments of the invention $R^5$ is selected from H, methyl and benzyl. In a preferred embodiment $R^1$ is H.

In another embodiment of the invention, compounds of Formula II include those in which $R^6$ is selected from H or an alkylene group which is bonded to $R^4$ to form the naphthalene ring skeleton. In a preferred embodiment of the invention, $R^6$ is H.

In specific embodiments of the invention, the compounds of Formula I and Formula II include:

2-[(4-t-butyl-2,6-dimethylphenyl)methyl]-4,5-dihydro-1H-imidazole;

2-[(4-t-butyphenyl)methyl]-4,5-dihydro-1H-imidazole;

4,5-dihydro-2-[(4-isopropylphenyl)methyl]-1H-imidazole;

2-[(4-bromo-2,6-dimethylphenyl)methyl]-4,5-dihydro-1H-imidazole;

4,5-dihydro-2-[(2,4,6-trimethylphenyl)methyl]-1H-imidazole;

4,5-dihydro-2-[(2,6-dimethyl4-isopropylphenyl)methyl]-1H-imidazole;

2-[(4-t-butyl-2-methylphenyl)methyl]-4,5-dihydro-1H-imidazole;

2-[(4-t-butyl-2,6-dimethylphenyl)methyl]-4,5-dihydro-1-methylimidazole;

2-[(4-t-butyl-2,6-dimethylphenyl)methyl]-1-benzyl-4,5-dihydroimidazole;

2-(4-t-butyl-2,6-dimethylbenzyl)-1,4,5,6-tetrahydropyrimidine;

4,5-dihydro-2-(2-naphthalenylmethyl)-1H-imidazole; and 4-t-butyl-2,6-dimethylbenzeneethanimidamide.

Preferred compounds of Formula I and II include:

2-[(4-t-butyl-2,6-dimethylphenyl)methyl]-4,5-dihydro-1H-imidazole;

2-[(4-t-butyphenyl)methyl]-4,5-dihydro-1H-imidazole;

2-[(4-bromo-2,6-dimethylphenyl)methyl]-4,5-dihydro-1H-imidazole;

4,5-dihydro-2-[(2,4,6-trimethylphenyl)methyl]-1H-imidazole;

4,5-dihydro-2-[(2,6-dimethyl4-isopropylphenyl)methyl]-1H-imidazole;

2-[(4-t-butyl-2,6-dimethylphenyl)methyl]-4,5-dihydro-1-methylimidazole;

2-[(4-t-butyl-2-methylphenyl)methyl]-4,5-dihydro-1H-imidazole;

2-[(4-t-butyl-2,6-dimethylphenyl)methyl]-1-benzyl4,5-dihydroimidazole;

2-(4-t-butyl-2,6-dimethylbenzyl)-1,4,5,6-tetrahydropyrimidine; and 4-t-butyl-2,6-dimethylbenzeneethanimidamide.

Particularly preferred compounds of Formula I and II include:

2-[(4-t-butyphenyl)methyl]4,5-dihydro-1H-imidazole;

2-[(4-bromo-2,6-dimethylphenyl)methyl]-4,5-dihydro-1H-imidazole;

4,5-dihydro-2-[(2,6-dimethyl-4-isopropylphenyl)methyl]-1H-imidazole;

2-[(4-t-butyl-2,6-dimethylphenyl)methyl]-4,5-dihydro-1-methylimidazole;

2-[(4-t-butyl-2,6-dimethylphenyl)methyl]-1-benzyl4,5-dihydroimidazole;

2-[(4-t-butyl-2-methylphenyl)methyl]4,5-dihydro-1H-imidazole;

2-(4-t-butyl-2,6-dimethylbenzyl)-1,4,5,6-tetrahydropyrimidine; and 4-t-butyl-2,6-dimethylbenzeneethanimidamide.

Most preferred compounds of Formula I and II include:

2-[(4-t-butyl-2-methylphenyl)methyl]-4,5-dihydro-1H-imidazole;

2-(4-t-butyl-2,6-dimethylbenzyl)-1,4,5,6-tetrahydropyrimidine; and 4-t-butyl-2,6-dimethylbenzeneethanimidamide.

Acid addition salts of the compound of Formula I and II are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I and II for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those established in the art. Therefore, compounds of Formula I and II wherein $R^1$ is a group of Formula i and $R^2$–$R^6$ and n are as defined above, can be prepared by coupling a reagent of Formula A with a reagent of Formula B in an alcoholic solvent such as ethanol at temperatures in the range of 25–100° C., preferably at from 50–80° C., as shown in the scheme below.

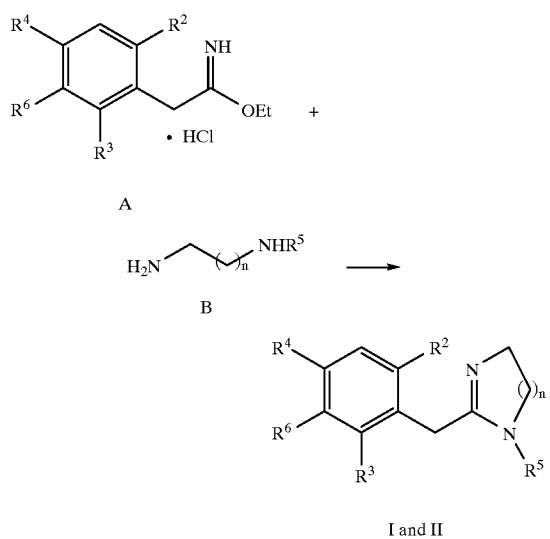

Compounds of Formula I wherein $R^1$ is a group of Formula ii can be prepared simply by reacting reagent A in a sealed tube with ammonia in an alcoholic solvent such as ethanol or methanol at temperatures in the range of 25° C. to 100° C. (preferably in methanol at a temperature of from 60–65° C.).

Reagents of Formula A can be prepared from the corresponding phenyl acetonitrile compound by treatment with ethanol in the presence of an appropriate acid such as hydrochloric acid in an inert solvent such as ether at temperatures in the range of 0° C. to 30° C., preferably 0° C. to 25° C. Reagents B are commercially available, and can be prepared using well established procedures known to one skilled in the art.

The phenyl acetonitrile precursors to Reagent A compounds are commercially available, and can be prepared from reagents of Formula C, wherein X is a leaving group such as a halogen or tosyl group, by treatment with sodium cyanide in a polar solvent at temperatures in the range of 50 to 100° C. Preferred conditions are ethanol/water (6:1) at temperatures in the range of 75–100° C.

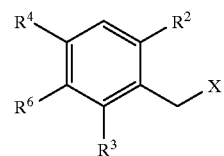

Reagents of Formula C are commercially available, and can be synthesized by established techniques, for example by treating the alcohol with halogenating reagents such as $CBr_4$ and triphenylphosphine (X=Br) or thionyl chloride (X=Cl) in inert solvents such as methylene chloride and benzene.

The above alcohol precursor to reagents of Formula C are also commercially available, and can be prepared by reduction of the corresponding aldehyde using metal hydride reducing reagents in inert solvents such as ethanol, ether and tetrahydrofuran, at temperatures in the range of 0–70° C. Preferred conditions for reduction of the aldehyde are sodium borohydride in ethanol at temperatures in the range of 30–60° C.

Most of the above aldehydes are commercially available, however, they also can be prepared from the corresponding amines by displacement of the diazonium salt, prepared by reaction of the amine with sodium nitrite in the presence of an acid such as hydrochloric acid, with paraformaldehyde.

In an embodiment of the invention, the compound is provided in labeled form, such as radiolabeled form, e.g. labeled by incorporation within its structure $^3H$ or $^{14}C$ or by conjugation to $^{125}I$. In another aspect of the invention, the compounds in labeled form can be used to identify 5-$HT_{1D\alpha}$ receptor ligands by techniques common in the art. This can be achieved by incubating the receptor in the presence of a ligand candidate and then incubating the resulting preparation with an equimolar amount of radiolabeled compound of the invention such as 2-(4-t-butyl-2,6-dimethylbenzyl)-1,4, 5,6 -tetrahydropyrimidine. 5-$HT_{1D\alpha}$ ligands are thus revealed as those that are not significantly displaced by the radiolabeled compound of the present invention. Alternatively, 5-$HT_{1D\alpha}$ ligand candidates may be identified by first incubating a radiolabeled form of a compound of the invention then incubating the resulting preparation in the presence of the candidate ligand. A more potent 5-$HT_{1D\alpha}$ ligand will, at equimolar concentration, displace the radiolabeled compound of the invention.

The receptor binding profile of the present compounds indicates their utility as pharmaceuticals for the treatment of various conditions in which the use of a 5-$HT_{1D\alpha}$ ligand is indicated, such as for the treatment of migraine, cluster headache and portal tension, a condition characterized by increased portal vein blood flow and typically associated with cirrhosis of the liver. The much reduced 5-$HT_{1D\beta}$ receptor binding of the present compounds indicates that their pharmaceutical use may not be associated with some of the unwanted side effects seen with the use of sumatriptan and other drugs with similar profiles.

For use in medicine, the compounds of the present invention can be administered in a standard pharmaceutical composition. The present invention therefore provides, in a further aspect, pharmaceutical compositions comprising a pharmaceutically acceptable carrier and a Formula I or II compound or a pharmaceutically acceptable salt, solvate or hydrate thereof, in an amount effective to stimulate the 5-$HT_{1D\alpha}$ receptor.

The compounds of the present invention may be administered by any convenient route, for example by oral, parenteral, buccal, sublingual, nasal, rectal or transdermal administration and the pharmaceutical compositions formulated accordingly.

Compounds of Formula I and II and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 1 to 25 mg) of a compound of Formula I or II or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous or intramuscular dose of between 0.1 mg and 100 mg, preferably between 0.1 mg and 50 mg, e.g., between 1 mg and 25 mg, of a compound of Formula I or II or a pharmaceutically acceptable salt, solvate or hydrate thereof calculated as the free base, the compound being administered 1 to 4 times per day. Suitably, the compounds will be administered for a period of continuous therapy, for example for a week or more.

EXAMPLE 1

2,6-Dimethyl-4-isopropylbenzaldehyde

A solution of $NaNO_2$ (1.75 g, 25 mmol) in water (4 mL) was added to a stirred solution of 2,6-dimethyl-4-isopropylaniline hydrochloride (Schubert, W. M. et al. J. Amer. Chem. Soc. 1954, 76:1) (5 g, 25 mmol) in concentrated HCl (4.5 mL) at 0° C. The mixture was allowed to stir at 0° C. for 1.5 hours. Potassium acetate (6 g) was then added. At the same time, a solution of paraformaldehyde (1.15 g), hydroxylamine hydrochloride (2.63 g, 37.84 mmol) and potassium acetate (5.1 g) in water (17 mL) was heated under reflux for 15 min. To this solution, cooled to 10–15° C., was added potassium acetate (16.5 g) in water (18 mL), copper sulfate (0.625 g) and sodium sulfite (0.1 g). The neutral diazonium solution was then added immediately to the paraformaldehyde mixture and the resulting solution was allowed to stir at room temperature for 2 hours. The mixture was acidified with 20 mL of concentrated HCl and heated at reflux for 2 hours. The cooled mixture was extracted with ether (3×30 mL) and the solvent was removed under reduced pressure. The yellow liquid was purified by column chromatography using as eluent hexane-EtOAc (97:3) to give 0.72 g (16%) of the title compound as a white liquid.

EXAMPLE 2a 2,6-Dimethyl4-isopropylbenzyl alcohol

A solution of sodium borohydride (0.04 g, 1.04 mmol) in 90% ethanol (5 mL) was added dropwise to a solution of 2,6-dimethyl4-isopropylbenzaldehyde (Example 1) (0.55 g, 3.1 mmol) in absolute ethanol (5 mL). The reaction mixture was allowed to stir at room temperature for 1 hour, then heated at 60° C. for 30 min. The solution was cooled to 0° C. and the unreacted sodium borohydride was decomposed by the addition of a few drops of 3N HCl. The solvent was removed under reduced pressure to give a red oil which was suspended in water (10 mL) and extracted with ether (2×20 mL). The solvent was removed under reduced pressure to afford a red oil which was purified by flash chromatography using silica gel (eluted with hexane-EtOAc, 93:3) to give 0.48 g (87%) of the title compound as a white solid; mp 75–77° C.

In a like manner, the following additional compound was prepared:
(b) 4Bromo-2,6-dimethylbenzyl alcohol, from 4-bromo-2,6-dimethylbenzaldehyde (Hjed, H. et al. Acta Chem. Scand. 1965, 19:2166); 95% yield, mp 117–119° C.

EXAMPLE 3a 2,6-Dimethyl-4-isopropylbenzyl chloride

Thionyl chloride (0.63 g, 5.28 mmol) was added to a solution of 2,6-dimethyl-4-isopropylbenzyl alcohol (Example 2a) (0.47 g, 2.64 mmol) in dry benzene (20 mL). The reaction mixture was allowed to stir at room temperature for 2 hours. The solvent was removed under reduced pressure to give a yellow oil. The crude oil was suspended in water (10 mL) and extracted with ether (3×10 mL). The solvent was removed under reduced pressure to give 0.51 g (98%) of the title compound as a white liquid.

In a like manner, the following additional compound was prepared:
(b) 4-Bromo-2,6-dimethylbenzyl chloride, from 4-bromo-2,6-dimethylbenzyl alcohol (Example 2b); white solid, 95% yield, mp 63–65° C.
(c) 4-t-Butyl-2-methylbenzylchloride, from 4-t-butyl-2-methylbenzyl alcohol (Baciocchi, E. et al. Tetrahedron, 1988, 44:6525).

EXAMPLE 4a 4-t-Butylphenylacetonitrile

Sodium cyanide (1.07 g, 22 mmol) was added to a stirred solution of 4-t-butylbenzylbromide (5 g, 22 mmol) in a mixture of EtOH-$H_2O$ (6:1) (70 mL). The reaction mixture was allowed to stir under reflux conditions for 4 hours. After cooling the mixture to room temperature, the solvent was evaporated under reduced pressure to afford a yellow oil. The oil was suspended in water (20 mL) and extracted with ether (3×25 mL). The solvent was removed under reduced pressure to give a yellow oil which was purified by distillation (Kugelrohr, bp 120–125° C., 0.2 mm Hg) to afford 3.37 g (89%) of the title compound as a colorless oil.

In a like manner the following addition compounds were prepared:
(b) 2,4,6-Trimethylphenylacetonitrile, from 2,4,6-trimethylbenzyl chloride.
(c) 2,6-Dimethyl-4-isopropylphenylacetonitrile, from 2,6-dimethyl-4-isopropylbenzyl chloride (Example 3a); 64% yield, mp 58–60° C.
(d) 4-Bromo-2,6-dimethylphenylacetonitrile, from 4-bromo-2,6-dimethylbenzyl chloride (Example 3b); white solid, 75% yield, mp 83–85° C.
(e) 4-t-Butyl-2-methylphenylacetonitrile, from 4-t-butyl-2-methylbenzylchloride (Example 3c); oil, bp 135–140° C.

EXAMPLE 5a 4,5-Dihydro-2-[(4-isopropylphenyl)methyl]-1H-imidazole Hydrochloride To a solution of 4-isopropylphenylacetonitrile (2 g, 12.5 mmol) in anhydrous ether (50 mL) was added absolute ethanol (0.5 g, 12.5 mmol) and an excess of HCl gas was passed into the solution with cooling in an ice bath. The resulting solution was allowed to stir at 0° C. for 1.5 hours and at room temperature overnight. The white solid was collected by filtration, washed with ether (2×20 mL) and dried to give 2.52 g (84%) of 4-isopropylphenylacetimidate hydrochloride as white crystals, mp 118–120° C. A solution of ethylenediamine (1.25 g, 20 mmol) in absolute ethanol (5 mL) was added to a solution of the imidate hydrochloride (2.5 g, 10 mmol) in absolute ethanol (15 mL) cooled at ice-bath temperature. After stirring at 0° C. for 1 hour, the solution was heated at reflux for 20 minutes. The solvent was evaporated and the oily residue was washed with water (2×3 mL) and extracted with methylene chloride (3×15 mL). The solution was dried ($MgSO_4$), filtered and evaporated under reduced pressure to afford 2 g of the free base of the title compound. A solution of the free base in anhydrous ether was treated with dry HCl gas. The crude salt was collected and recrystallized from ethanol/ether to give 1.95 g (79%) of the title compound as a white solid. mp 176–178° C.; Anal. $C_{13}H_{18}N_2$.HCl: C, H, N.

In a like manner, the following additional compounds were prepared:
(b) 2-[(4-t-Butyphenyl)methyl]-4,5-dihydro-1H-imidazole hydrochloride, from 4-t-butylphenylacetonitrile (Example 4a); white crystals, mp 232–234° C., Anal. $C_{14}H_{20}N_2$.HCl: C, H, N.
(c) 2-[(4-t-Butyl-2,6-dimethylphenyl)methyl]-4,5-dihydro-1H-imidazole hydrochloride, from 4-t-butyl-2,6-dimethylphenylacetonitrile (Bun-Hoi et al. Bull. Soc. Chim. 1942, 9:889); white solid, mp 327–329° C.
(d) 2-[(4-Bromo-2,6-dimethylphenyl)methyl]-4,5-dihydro-1H-imidazole hydrochloride, from 4-bromo-2,6-dimethylphenylacetonitrile (Example 4d); white solid, mp 293–295° C., Anal. $C_{12}H_{15}BrN_2$.HCl: C, H, N.
(e) 4,5-Dihydro-2-[(2,4,6-trimethylphenyl)methyl]-1H-imidazole hydrochloride, from 2,4,6-trimethylphenylacetonitrile (Example 4b); white solid, 63% yield, mp 274–276° C.
(f) 4,5-Dihydro-2[(2,6-dimethyl4-isopropylphenyl)methyl]-1H-imidazole hydrochloride, from 2,6-dimethyl-4-isopropylphenylacetonitrile (Example 4c); white solid, 65% yield, mp 296–298° C., Anal. $C_{15}H_{22}N_2$.HCl.0.1 $H_2O$: C, H, N.
(g) 4,5-Dihydro-2-(2-naphthalenylmethyl)-1H-imidazole hydrochloride, from 2-naphthylacetonitrile; white crystals, 75% yield, mp 278–280° C., Anal. $C_{14}H_{14}N_2$.HCl: C, H, N.
(h) 2-[(4-t-Butyl-2,6-dimethylphenyl)methyl]-4,5-dihydro-1-methylimidazole hydrochloride, from 4-t-butyl-2,6-dimethylphenylacetonitrile (Bun-Hoi et al. Bull. Soc. Chim. 1942, 9:889) and N-methylethylenediamine; white solid, 73% yield, mp 250–252° C., Anal. $C_{17}H_{26}N_2$.HCl: C, H, N.
(i) 2-[(4-t-Butyl-2,6-dimethylphenyl)methyl]-1-benzyl-4,5-dihydroimidazole hydrochloride, from 4-t-butyl-2,6-dimethylphenylacetonitrile and N-benzylethylenediamine; white solid, 68% yield, mp 216–218° C., Anal. $C_{23}H_{30}N_2$.HCl: C, H, N.
(j) 2-(4-t-Butyl-2,6-dimethylbenzyl)-1,4,5,6-tetrahydropyrimidine hydrochloride, from 4-t-butyl-2,6-dimethylphenylacetonitrile and 1,3-diaminopropane; white crystals, 71 % yield, mp 289–291° C., Anal. $C_{17}H_{26}N_2$.HCl: C, H, N.
(k) 2-[(4-t-Butyl-2-methylphenyl)methyl]-4,5-dihydro-1H-imidazole hydrochloride, from 4-t-butyl-2-methylphenylacetonitrile (Example 4e); white solid, mp 255° C., Anal. $C_{15}H_{22}N_2$.HCl.0.25$H_2O$: C, H, N.

EXAMPLE 6

4-t-Butyl-2,6-dimethylbenzeneethanimidamide

To a solution of 4-t-butyl-2,6-dimethylphenylacetonitrile (Bun-Hoi et aL. Bull. Soc. Chim. 1942, 9:889) (1.45 g, 7.21 mmol) in anhydrous ether (20 mL) was added absolute ethanol (0.33 g, 7.21 mmol). An excess of HCl gas was passed into the solution with cooling in an ice bath. The resulting solution was allowed to stir at 0° C. for 1.5 hours and at room temperature overnight. The white solid was collected by filtration, washed with ether (2×20 mL) and dried to give 0.89 g (44%) of 4-t-butyl-2,6-dimethylphenylacetimidate. The imidate (0.302 g, 1.06 mmol) was dissolved in ethanol (6 mL) and ammonia (gas, excess) was bubbled through the solution for 30–40 minutes. The reaction vessel was sealed and stirred at room temperature for 36 hours and then at 60–65° C. for 45 minutes. After cooling to room temperature, the reaction mixture was filtered through celite, rinsing with methanol. The solvent was removed under reduced pressure and the residue redissolved in chloroform (100 mL), washed with 2M NaOH (10 mL), dried over sodium sulfate and evaporated to dryness. The residue was redissolved in methylene chloride and HCl (2M in ether, 2 mL) was added and the mixture stirred for 10 minutes. The solvent was removed under reduced pressure and the residue dissolved in ethanol (1 mL). Ether (15 mL) was added and the resulting crystals, collected to provide the title compound as its hydrochloride salt (203 mg, 75%). mp 224–226° C.

EXAMPLE 7

Comparison of the Binding Affinities

Compounds of the previous examples, as well as reference compounds were evaluated for binding affinity using cell types receptive specifically to 5-$HT_{1D\alpha}$ and 5-$HT_{1D\beta}$ ligands. The assay protocol generally entailed the incubation of membranes prepared from cells expressing the 5-$HT_{1D\alpha}$ ) or 5-$HT_{1D\beta}$ subtype of 5-HT receptors with $^3$H-serotonin. Increasing concentrations of the test compound were incubated with the radioligand and the membrane homogenates prepared from the recombinant cells. After a 60 minute incubation at 22° C., the incubation was terminated by vacuum filtration. The filters were washed with buffer and counted for radioactivity using liquid scintillation spectroscopy. The affinity of the test compound for the 5-$HT_{1D\alpha}$ or 5-$HT_{1D\beta}$ receptor was determined by computer-assisted analysis of the data and by determining the amount of compound necessary to inhibit 50% of the binding of the radioligand to the receptor. Concentrations ranging from $10^{-11}$ M to $10^{-5}$ M of the test compound were evaluated. For comparison, the arylimidazoline known as oxymetazoline was also evaluated (the binding affinity of this compound for various 5-HT receptors has been reported; see Schoeffter and Hoyer, Eur. J. Pharm. 1991, 196:213). The results are presented in Table 1 below.

TABLE 1

Comparison of Binding Affinities

| Compound | Example # | 5-$HT_{1D\alpha}$ $K_i$ (nM) | 5-$HT_{1D\beta}$ $K_i$ (nM) | $\frac{5\text{-}HT_{1D\beta}}{5\text{-}HT_{1D\alpha}}$ |
|---|---|---|---|---|
| (structure) | oxymetazoline | 0.36 | 0.33 | 1 |
| (structure) | 5c | 0.73 | 14.9 | 20 |
| (structure) | 5b | 105 | >10,000 | >95 |
| (structure) | 5d | 74 | 1568 | 21 |
| (structure) | 5e | 92 | 3480 | 20 |

TABLE 1-continued
Comparison of Binding Affinities
| Compound | Example # | 5-HT$_{1D\alpha}$ K$_i$ (nM) | 5-HT$_{1D\beta}$ K$_i$ (nM) | $\frac{\text{5-HT}_{1D\beta}}{\text{5-HT}_{1D\alpha}}$ |
|---|---|---|---|---|
| 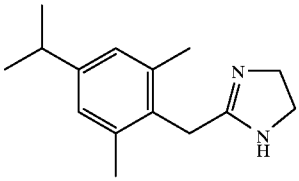 | 5f | 1.6 | 37 | 23 |
| 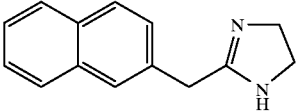 | 5g | 135 | 1165 | 9 |
| 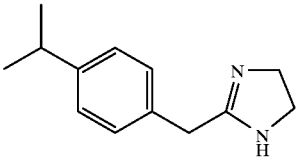 | 5a | 340 | 2780 | 8 |
| 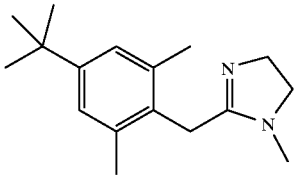 | 5h | 86 | >5000 | >58 |
| 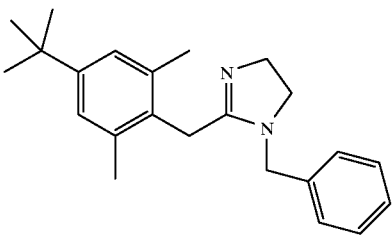 | 5i | 30 | 1862 | 62 |
| 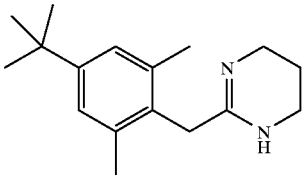 | 5j | 35 | >5000 | >143 |
| 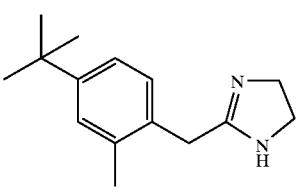 | 5k | 6.8 | 712 | 105 |

EXAMPLE 8

Agonist Assay

The in vitro evaluation of the 5-$HT_{1D}$ receptor agonist activity of the compounds of the invention was carried our by testing the extent to which they mimic sumatriptan in contracting the rabbit saphenous vein (Perez, M. et al. J. Med. Chem. 1995, 38:3602–3607).

Tissues were obtained from male New Zealand White rabbits (~3–4 kg) which were sacrificed by an overdose of pentobarbital. The saphenous veins from both the left and right side were cleaned of fat and connective tissue and placed in Krebs solution (118 mM NaCl, 11 mM glucose, 25 mM $NaHCO_3$, 4.7 mM KCl, 2.5 mM $CaCl_2.2H_2O$, 1.2 mM $KH_2PO_4$, and 1.2 mM $MgSO_4.7H_2O$. Ring segments of the vein (4–5 mm in length) were cut and the endothelium gently removed. The segments were mounted in 10 mL baths containing Krebs buffer and were constantly aerated with 95% oxygen/5% carbon dioxide and maintained at 37° C. and pH 7.4 in order to record the isometric tension. A resting tension of 2.5 g was applied and the tissues allowed to equilibrate for 90 minutes, with washing every 15–20 minutes. After the equilibrium period, the rings were depolarized by the addition of two aliquots of KCl (80 mM final concentration) separated by a 20 minute washing period. The tissues were then exposed to prazosin, idazoxan and indomethacin (all 1 μM final concentration) for 30 minutes in order to exclude the actions of $\alpha_1$- and $\alpha_2$-adrenergic receptors and prostaglandin receptors respectively. Cumulative concentration-effect curves were then constructed for sumatriptan and the test compounds. Responses were calculated as a percentage of the maximal contraction evoked by 80 mM KCl. Only one compound was tested per preparation.

The following Table illustrates the in vitro activities for the compounds of the invention on the rabbit isolated saphenous vein. $EC_{50}$ represents the concentration of the compound which causes 50% of the maximum contraction effected by it. If the compound induced a maximum contraction of less than 60% of that of KCl (80 mM), it was considered a partial agonist.

| Compound | $EC_{50}$ (μM) |
| --- | --- |
| sumatriptan | 0.22 |
| 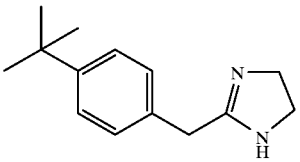 | 2.9 |
| 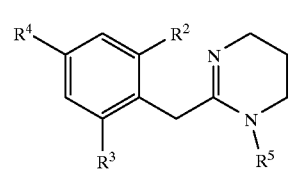 | 0.1 |
| | 0.023 |

We claim:

1. A compound according to the formula:

III

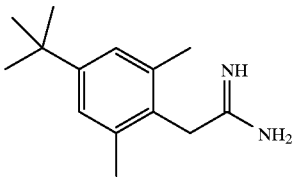

wherein either (a) $R^2$ and $R^3$ are both $C_1$–$C_6$ alkyl, or (b) one of $R^2$ and $R^3$ is $C_1$–$C_6$ alkyl and the other is H;

$R^4$ is selected from $C_2$–$C_6$ alkyl, halo, phenyl, amino and nitro;

$R^5$ is selected from H, $C_1$–$C_6$ alkyl and benzyl;

or a salt or a hydrate thereof.

2. A compound according to claim 1 wherein $R^2$ and $R^3$ are both methyl.

3. A compound according to claim 1 wherein $R^4$ is t-butyl.

4. A compound according to claim 1 which is 2-(4-t-butyl-2,6-dimethylbenzyl)-1,4,5,6-tetrahydropyrimidine.

5. A compound according to claim 1, wherein one of $R^2$ and $R^3$ is methyl and the other is H.

6. A compound according to claim 1, wherein $R^4$ is selected from $C_2$–$C_6$ alkyl, phenyl and amino.

7. A compound according to claim 6, wherein $R^4$ is selected from t-butyl and isopropyl.

8. A compound according to claim 1, wherein $R^5$ is selected from H, methyl and benzyl.

* * * * *